United States Patent [19]

Shepard et al.

[11] Patent Number: 4,840,963

[45] Date of Patent: Jun. 20, 1989

[54] 2-SULFAMOYL-1H-INDOLE DERIVATIVES FOR THE TREATMENT OF ELEVATED INTRAOCULAR PRESSURE

[75] Inventors: Kenneth L. Shepard, North Wales; Samuel L. Graham, Harleysville, both of Pa.

[73] Assignee: Merck & Co., Inc., Rahway, N.J.

[21] Appl. No.: 679,431

[22] Filed: Dec. 7, 1984

Related U.S. Application Data

[63] Continuation-in-part of Ser. No. 589,385, Mar. 14, 1984, abandoned.

[51] Int. Cl.[4] ............... A61K 31/40; C07D 209/10
[52] U.S. Cl. ............................ 514/418; 544/143; 544/405; 546/201; 546/273; 548/237; 548/336; 548/430; 548/486; 548/494
[58] Field of Search ............... 548/486, 494; 514/418

[56] References Cited

U.S. PATENT DOCUMENTS

| | | |
|---|---|---|
| 4,386,098 | 5/1983 | Woltersdorf . |
| 4,416,890 | 11/1983 | Woltersdorf et al. ............... 548/166 |
| 4,419,121 | 12/1983 | Meyer et al. ............... 71/92 |
| 4,425,153 | 1/1984 | Adams ............... 71/92 |
| 4,426,388 | 1/1984 | Woltersdorf ............... 548/166 |
| 4,454,148 | 6/1984 | Woltersdorf . |
| 4,456,599 | 6/1984 | Woltersdorf . |
| 4,470,991 | 9/1984 | Woltersdorf . |
| 4,472,417 | 9/1984 | Woltersdorf . |
| 4,472,418 | 9/1984 | Woltersdorf . |
| 4,499,103 | 2/1985 | DeSolms ............... 548/167 |

FOREIGN PATENT DOCUMENTS

| | | |
|---|---|---|
| 0070698 | of 0000 | European Pat. Off. . |
| 82108 | 6/1983 | European Pat. Off. ............... 71/92 |
| 2081712 | of 0000 | United Kingdom . |

*Primary Examiner*—Donald G. Daus
*Assistant Examiner*—Frederick Tsung
*Attorney, Agent, or Firm*—William H. Nicholson; Michael C. Sudol, Jr.

[57] ABSTRACT

Novel 2-sulfamoyl-1H-indoles and derivatives thereof are shown to be useful for the treatment of elevated intraocular pressure in pharmaceutical compositions designed for systemic or topical ophthalmic administration.

2 Claims, No Drawings

2-SULFAMOYL-1H-INDOLE DERIVATIVES FOR THE TREATMENT OF ELEVATED INTRAOCULAR PRESSURE

This is a continuation-in-part of copending application Ser. No. 589,385, filed Mar. 14, 1984, now abandoned.

SUMMARY OF THE INVENTION

This invention relates to novel 2-sulfamoyl-1H-indoles which are useful in the reduction of elevated intraocular pressure. More particularly this invention relates to compounds having the structural formula:

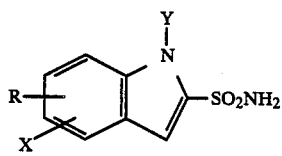

wherein R, X and Y are as hereinafter defined, as well as the pharmaceutically and ophthalmologically acceptable salts thereof. This invention also relates to pharmaceutical compositions for systemic and ophthalmic use employing a novel compound of this invention as active ingredient for the treatment of elevated intraocular pressure, especially when accompanied by pathological damage such as in the disease known as glaucoma.

BACKGROUND OF THE INVENTION

Glaucoma is an ocular disorder associated with elevated intraocular pressures which are too high for normal function and may result in irreversible loss of visual function. If untreated, glaucoma may eventually lead to blindness. Ocular hypertension, i.e., the condition of elevated intraocular pressure without optic nerve head damage or characteristic glaucomatous visual field defects, is now believed by many ophthalmologists to represent the earliest phase of glaucoma.

Many of the drugs formerly used to treat glaucoma proved not entirely satisfactory. Indeed, few advances were made in the treatment of glaucoma since pilocarpine and physostigmine were introduced. Only recently have clinicians noted that many β-adrenergic blocking agents are effective in reducing intraocular pressure. While many of these agents are effective in reducing intraocular pressure, they also have other characteristics, e.g. membrane stabilizing activity, that are not acceptable for chronic ocular use. (S)-1-tert-Butylamino-3-[(4-morpholino-1,2,5-thiadiazol-3-yl)oxy]-2-propanol, a β-adrenergic blocking agent, was found to reduce intraocular pressure and to be devoid of many unwanted side effects associated with pilocarpine and, in addition, to possess advantages over many other β-adrenergic blocking agents, e.g. to be devoid of local anesthetic properties, to have a long duration of activity, and to display minimal tolerance.

Although pilocarpine, physostigmine and the β-blocking agents mentioned above reduce intraocular pressure, none of these drugs manifests its action by inhibiting the enzyme carbonic anhydrase and, thereby, impeding the contribution to aqueous humor formation made by the carbonic anhydrase pathway.

Agents referred to as carbonic anhydrase inhibitors, block or impede this inflow pathway by inhibiting the enzyme, carbonic anhydrase. While such carbonic anhydrase inhibitors are now used to treat intraocular pressure by oral, intravenous or other systemic routes, they thereby have the distinct disadvantage of inhibiting carbonic anhydrase throughout the entire body. Such a gross disruption of a basic enzyme system is justified only during an acute attack of alarmingly elevated intraocular pressure, or when no other agent is effective. Despite the desirability of directing the carbonic anhydrase inhibitor only to the desired ophthalmic target tissue, no topically effective carbonic anhydrase inhibitors are available for clinical use.

However, topically effective carbonic anhydrase inhibitors are reported in European Patent applications Nos. 0,070,239 and 0,079,269 and U.S. application, Ser. No. 364,953, now U.S. Pat. No. 4,426,388. The compounds reported therein are 5 (and 6)-hydroxy-2-benzothiazolesulfonamides and acyl esters thereof.

To be an effective and acceptable topical agent, an ophthalmic carbonic anhydrase inhibitor must not only penetrate the ophthalmic tissues to reach the active sites within the eye, but it must also be devoid of those side effects including irritation, allergic reaction and the like which would militate against long term administration.

DETAILED DESCRIPTION OF THE INVENTION

The novel compounds of this invention have the structural formula:

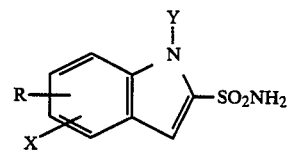

or an ophthalmologically or pharmaceutically acceptable salt thereof, wherein:

X is hydrogen, halo, such as chloro, bromo or fluoro, $C_{1-3}$alkyl, hydroxy or $C_{1-3}$alkoxy; and Y is hydrogen or $C_{1-3}$ alkyl;

R is:
(1) hydroxy,
(2) $R_a{}^1$ wherein $R_a{}^1$ is
  (a) $C_{1-18}$ alkyl either straight or branched chain and substituted with one or more of
    (i) $C_{3-6}$ cycloalkyl,
    (ii) halo, such as chloro, bromo or fluoro,
    (iii) aryl, wherein the aryl group is carbocyclic such as phenyl or naphthyl, or heterocyclic such as pyridinyl, furanyl, pyrazinyl, morpholinyl, oxazolinyl, dioxolinonyl, imidazolyl, thienyl or the like and wherein the aryl group can be substituted with one or more of $C_{1-10}$ alkyl, halo, $C_{1-4}$ alkoxy or $C_{2-5}$ alkanoyl,
    (iv) hydroxy,
    (v) $C_{1-3}$ alkoxy,
    (vi) aryl-$C_{1-3}$ alkoxy,
    (vii) amino,
    (viii) ($C_{1-3}$ alkyl)amino,
    (ix) di($C_{1-3}$ alkyl)amino,
    (x)

wherein $R^2$ is (1) HO—,
(2) M+O—, wherein M³⁰ is a pharmaceutically acceptable cation such as that from an alkali metal, or an ammonium,
(3) $C_{1-10}$ alkoxy,
(4) R³R⁴N— wherein R³ and R⁴ are independently hydrogen, $C_{1-15}$ alkyl, or taken together form a 3–7 membered heterocycle with the nitrogen to which they are attached such as piperidino or pyrrolidino;
(b) $C_{3-6}$ cycloalkyl,
(c) $C_{1-18}$ alkyl-$C_{3-6}$ cycloalkyl,
(d) aryl as previously defined,
(e) $C_{2-6}$ alkenyl,
(f) aryl-$C_{2-6}$ alkenyl,
(g) $C_{2-6}$ alkynyl,
(3) $R_a^1$—O—,
(4)

wherein $R^1$ is $R_a^1$ or $C_{1-18}$ alkyl
(5)

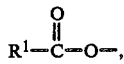

(6)

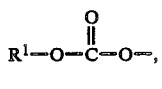

(7)

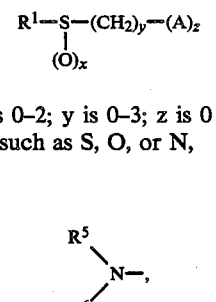

wherein x is 0–2; y is 0–3; z is 0 or 1; and A is a heteroatom such as S, O, or N,
(8)

where R⁵ and R⁶ are independently:
(a) hydrogen,
(b) $C_{1-18}$ alkyl, either straight or branched chain,
(c) $C_{3-6}$ cycloalkyl,
(d) $C_{3-6}$ cycloaklyl-$C_{1-3}$ alkyl,
(e) aryl-$C_{1-3}$ alkyl wherein the aryl group is either unsubstituted or substituted with one or more of chloro, bromo, fluoro, $C_{1-3}$ alkyl or $C_{1-3}$ alkoxy,
(f)

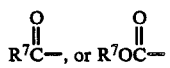

wherein R⁷ is
(i) $C_{1-18}$ alkyl, either straight or branched chain, (ii) aryl, either unsubstituted or substituted with one or more of chloro, bromo, fluoro, $C_{1-3}$ alkyl, or $C_{1-3}$ alkoxy,
(iii) aryl-$C_{1-3}$ alkyl wherein the aryl group is either unsubstituted or substituted with one or more of chloro, bromo, fluoro, $C_{1-3}$ alkyl or $C_{1-3}$ alkoxy,
(iv) amino-$C_{1-18}$ alkyl either straight or branched chain; or
(9) R⁵ and R⁶ if lower alkyl, are joined together directly or through a heteroatom selected from O or N to form a 5 to 6 membered heterocycle with the nitrogen to which they are attached such as pyrrolidine, piperidine, morpholine, or piperazine.
(9)

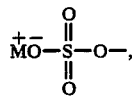

wherein M+ is an ophthalmologically acceptable cation selected from sodium, potassium, ammonium, tetra($C_{1-4}$alkyl)ammonium, pyridinium, imidazolium, pralidoxime, and thiamine
(10)

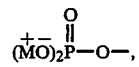

wherein M+ is as previously defined;
(11) M+O—–P⁰—O—, wherein R⁸ is $C_{1-3}$ alkyl or OR⁸ phenyl —$C_{1-3}$ alkyl; or
(12)

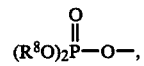

wherein R⁸ is as previously defined, and the two may be the same or different; and R and X joined together represent methylenedioxy.

In the preferred embodiments of this invention, X is hydrogen and R is HO—,

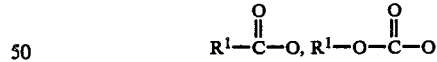

or R⁵R⁶N—, especially wherein R¹ is $C_{1-18}$alkyl, and more especially $C_{1-5}$alkyl. It is also preferred that the substituent R be in the 5- or 6-position of the indole, especially the 5-position.

Preferred species of this invention are:
5(or 6)-hydroxy-2-sulfamoyl-1H-indole;
5(or 6)-(2-sulfamoyl-1H-indolyl)acetate;
5(or 6)-(2-sulfamoyl-1H-indolyl)2,2-dimethylpropionate;
5(or 6)-(2-sulfamoyl-1H-indolyl)2-methylpropionate;
5(or 6)-(2-sulfamoyl-1H-indolyl)3-ethoxycarbonylpropionate.

Representative carbonic anhydrase inhibitors of this invention include:
5(or 6)-hydroxy-2-sulfamoyl-1H-indole;
5(or 6)-(2-sulfamoyl-1H-indolyl)benzoate;
5(or 6)-(2-sulfamoyl-1H-indolyl)propionate;

5(or 6)-(2-sulfamoyl-1H-indolyl)butyrate;
5(or 6)-(2-sulfamoyl-1H-indolyl)2,2-dimethylpropionate;
5(or 6)-(2-sulfamoyl-1H-indolyl)octanoate;
5(or 6)-(2-sulfamoyl-1H-indolyl)dodecanoate;
5(or 6)-(2-sulfamoyl-1H-indolyl)4,4-dimethylcyclohexane carboxylate;
5(or 6)-(2-sulfamoyl-1H-indolyl)3-chloro-2,2-dimethylpropionate;
5(or 6)-(2-sulfamoyl-1H-indolyl)4-methylbenzoate;
5(or 6)-(2-sulfamoyl-1H-indolyl)4-chlorobenzoate;
5(or 6)-(2-sulfamoyl-1H-indolyl)4-methoxybenzoate;
5(or 6)-(2-sulfamoyl-1H-indolyl)2-(4-chlorophenyl)acetate;
5(or 6)-(2-sulfamoyl-1H-indolyl)3-(4-ethylphenyl)propionate;
5(or 6)-(2-sulfamoyl-1H-indolyl)3-hydroxy-2,2-dimethylpropionate;
5(or 6)-(2-sulfamoyl-1H-indolyl)4-aminobutyrate HCl;
5(or 6)-(2-sulfamoyl-1H-indolyl)acrylate;
5(or 6)-(2-sulfamoyl-1H-indolyl)crotonate;
5(or 6)-(2-sulfamoyl-1H-indolyl)propiolate;
5(or 6)-(2-sulfamoyl-1H-indolyl)3-phenyl-2-propenoate;
5(or 6)-(2-sulfamoyl-1H-indolyl)cyclopentaneacetate;
5(or 6)-2-sulfamoyl-1H-indolyl)phenylacetate;
5(or 6)-(2-sulfamoyl-1H-indolyl)cyclohexanecarboxylate;
5(or 6)-(2-sulfamoyl-1H-indolyl)acetate;
5(or 6)-(2-sulfamoyl-1H-indolyl)3-carboxypropionate;
5(or 6)-(2-sulfamoyl-1H-indolyl)3-carboxypropionate, sodium salt;
5(or 6)-(2-sulfamoyl-1H-indolyl)2-ethoxycarbonylacetate;
5(or 6)-(2-sulfamoyl-1H-indolyl)acetoacetate;
5(or 6)-(2-sulfamoyl-1H-indolyl)3-aminocarbonylpropionate;
5(or 6)-(2-sulfamoyl-1H-indolyl)N-acetylpiperidine-4-carboxylate;
5(or 6)-(2-sulfamoyl-1H-indolyl)nicotinoate;
5(or 6)-(2-sulfamoyl-1H-indolyl)1-methyl-4-imidazolylacetate;
5(or 6)-(2-sulfamoyl-1H-indolyl)2-methoxybutyrate;
5(or 6)-(2-sulfamoyl-1H-indolyl)2-methoxysuccinate;
5(or 6)-(2-sulfamoyl-1H-indolyl)phenyl carbonate;
5(or 6)-(2-sulfamoyl-1H-indolyl)ethyl carbonate;
5(or 6)-(2-sulfamoyl-1H-indolyl)propyl carbonate;
5(or 6)-(2-sulfamoyl-1H-indolyl)1,1-dimethylethyl carbonate;
5(or 6)-(2-sulfamoyl-1H-indolyl)n-heptyl carbonate;
5(or 6)-(2-sulfamoyl-1H-indolyl)undecanyl carbonate;
5(or 6)-(2-sulfamoyl-1H-indolyl)4,4-dimethylcyclohexyl carbonate;
5(or 6)-(2-sulfamoyl-1H-indolyl)2-chloro-1,1-dimethylethyl carbonate;
5(or 6)-(2-sulfamoyl-1H-indolyl)4-methylphenyl carbonate;
5(or 6)-(2-sulfamoyl-1H-indolyl)4-chlorophenyl carbonate;
5(or 6)-(2-sulfamoyl-1H-indolyl)4-methoxyphenyl carbonate;
5(or 6)-(2-sulfamoyl-1H-indolyl)-4-chlorobenzyl carbonate;
5(or 6)-(2-sulfamoyl-1H-indolyl)2-(4-ethylphenyl)ethyl carbonate;
5(or 6)-(2-sulfamoyl-1H-indolyl)2-methylpropyl carbonate;
5(or 6)-(2-sulfamoyl-1H-indolyl)allyl carbonate;
5(or 6)-(2-sulfamoyl-1H-indolyl)2-propynyl carbonate;
5(or 6)-(2-sulfamoyl-1H-indolyl)3-phenyl-2-propenyl carbonate;
5(or 6)-(2-sulfamoyl-1H-indolyl)cyclopentylmethyl carbonate;
5(or 6)-(2-sulfamoyl-1H-indolyl)benzyl carbonate;
5(or 6)-(2-sulfamoyl-1H-indolyl)cyclohexyl carbonate;
5(or 6)-(2-sulfamoyl-1H-indolyl)methyl carbonate;
5(or 6)-amino-2-sulfamoyl-1H-indole;
5(or 6)-ethylamino-2-sulfamoyl-1H-indole;
5(or 6)-diethylamino-2-sulfamoyl-1H-indole;
5(or 6)-[(1-methylethyl)amino]-2-sulfamoyl-1H-indole;
5(or 6)-[N-ethyl-N-(2-propyl)amino]-2-sulfamoyl-1H-indole;
5(or 6)-[(N-benzyl-N-ethyl)amino]-2-sulfamoyl-1H-indole;
5(or 6)-cyclohexylamino-2-sulfamoyl-1H-indole;
5(or 6)-cyclopentylmethylamino-2-sulfamoyl-1-indole;
5(or 6)-pivaloylamino-2-sulfamoyl-1H-indole;
5(or 6)-[(N-methyl-N-pivaloyl)amino]-2-sulfamoyl-1H-indole;
5(or 6)-pivaloyloxycarbonylamino-2-sulfamoyl-1H-indole;
5(or 6)-acetylamino-2-sulfamoyl-1H-indole;
5(or 6)-butyrylamino-2-sulfamoyl-1H-indole;
5(or 6)-benzoylamino-2-sulfamoyl-1H-indole;
5(or 6)-[(4-methylbenzoyl)amino]-2-sulfamoyl-1H-indole;
5(or 6)-[(4-fluorobenzoyl)amino]-2-sulfamoyl-1H-indole;
5(or 6)-(4-methoxybenzoyl)amino-2-sulfamoyl-1H-indole;
5(or 6)-nicotinoylamino-2-sulfamoyl-1H-indole;
5(or 6)-thienylcarbonylamino-2-sulfamoyl-1H-indole;
5(or 6)-alanylamino)-2-sulfamoyl-1H-indole;
5(or 6)-(N-ethyl-N-hydroxy)amino-2-sulfamoyl-1H-indole;
5(or 6)-(N-ethyl-N-methoxy)amino-2-sulfamoyl-1H-indole;
5(or 6)-(1-morpholino)-2-sulfamoyl-1H-indole;
2-sulfamoyl-1H-indole-6(or 5)-acetic acid;
2-sulfamoyl-1H-indole-6(or 5)-propionic acid;
5(or 6)-(2-hydroxyethyl)-2-sulfamoyl-1H-indole;
5(or 6)-(2,3-dihydroxypropoxy)-2-sulfamoyl-1H-indole;
5(or 6)-(dioxolin-2-one-4-ylmethoxy)-2-sulfamoyl-1H-indole;
5(or 6)-(5-oxazolinylmethoxy)-2-sulfamoyl-1H-indole;
5(or 6)-(1-methylimidazol-4-yloxy)-2-sulfamoyl-1H-indole;
5(or 6)-furfuryl-2-sulfamoyl-1H-indole;
5(or 6)-(2-morpholinylethyl)-2-sulfamoyl-1H-indole;
5(or 6)-morpholinylmethyl-2-sulfamoyl-1H-indole;
5(or 6)-hydroxymethyl-2-sulfamoyl-1H-indole;
5(or 6)-(acetyloxymethyl)-2-sulfamoyl-1H-indole;
5(or 6)-(2-acetyloxyethyl)-2-sulfamoyl-1H-indole;
5(or 6)-benzoyl-2-sulfamoyl-1H-indole;
5(or 6)-propionyl-2-sulfamoyl-1H-indole;
5(or 6)-butyryl-2-sulfamoyl-1H-indole;
5(or 6)-(2,2-dimethylpropionyl)-2-sulfamoyl-1H-indole;
5(or 6)-octanoyl-2-sulfamoyl-1H-indole;
5(or 6)-dodecanoyl-2-sulfamoyl-1H-indole;
5(or 6)-(4,4-dimethylcyclohexanecarbonyl)-2-sulfamoyl-1H-indole;
5(or 6)-(3-chloro-2,2-dimethylpropionyl)-2-sulfamoyl-1H-indole;
5(or 6)-(2-methylbenzoyl)-2-sulfamoyl-1H-indole;
5(or 6)-(4-chlorobenzoyl)-2-sulfamoyl-1H-indole;
5(or 6)-(4-methoxybenzoyl)-2-sulfamoyl-1H-indole;
5(or 6)-(4-chlorophenylacetyl)-2-sulfamoyl-1H-indole;

5(or 6)-[3-(4-ethylphenyl)propionyl)]-2-sulfamoyl-1H-indole;
5,6-dihydroxy-2-sulfamoyl-1H-indole;
5,6-dimethoxy-2-sulfamoyl-1H-indole;
5-hydroxy-6-methoxy-2-sulfamoyl-1H-indole;
6-hydroxy-5-methoxy-2-sulfamoyl-1H-indole; and
5,6-methylenedioxy-2-sulfamoyl-1H-indole;
5(or 6)-(3-hydroxy-2,2-dimethylpropionyl)-2-sulfamoyl-1H-indole;
5(or 6)-(4-aminobutyryl)-2-sulfamoyl-1H-indole;
5(or 6)-(acryloyl)-2-sulfamoyl-1H-indole;
5(or 6)-(crotonyl)-2-sulfamoyl-1H-indole;
5(or 6)-propiolyl-2-sulfamoyl-1H-indole;
5(or 6)-(3-phenyl-2-propenoyl)-2-sulfamoyl-1H-indole;
5(or 6)-cyclopentaneacetyl-2-sulfamoyl-1H-indole;
5(or 6)-phenylacetyl-2-sulfamoyl-1H-indole;
5(or 6)-cyclohexanecarbonyl-2-sulfamoyl-1H-indole;
5(or 6)-acetyl-2-sulfamoyl-1H-indole;
5(or 6)-(3-carboxypropionyl)-2-sulfamoyl-1H-indole;
5(or 6)-ethoxycarbonylacetyl-2-sulfamoyl-1H-indole;
5(or 6)-acetoacetyl-2-sulfamoyl-1H-indole;
5(or 6)-(3-aminocarbonylpropionyl)-2-sulfamoyl-1H-indole;
5(or 6)-(N-acetylpiperidine-4-carbonyl)-2-sulfamoyl-1H-indole;
5(or 6)-(4-imidazolyl)-2-sulfamoyl-1H-indole;
5(or 6)-pyrazinyl-2-sulfamoyl-1H-indole;
5(or 6)-(4-imidazolylcarbonyl)-2-sulfamoyl-1H-indole;
5(or 6)-(4-imidazolylsulfonyl)-2-sulfamoyl-1H-indole;
5(or 6)-(trifluoromethylsulfonyl)-2-sulfamoyl-1H-indole.

The novel process for preparing the compounds wherein R is hydroxy comprises treatment of a methoxy-2-sulfamoyl-1H-indole with at least an equimolar amount of pyridine hydrochloride at a temperature from about the fusion point to about 200° C., and preferably from about 160°–170° C. for from about 0.25 to 4 hours, preferably about 0.5 hour, until the reaction is substantially complete.

The novel process to prepare those compounds wherein R is

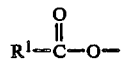

is represented by the following reaction scheme:

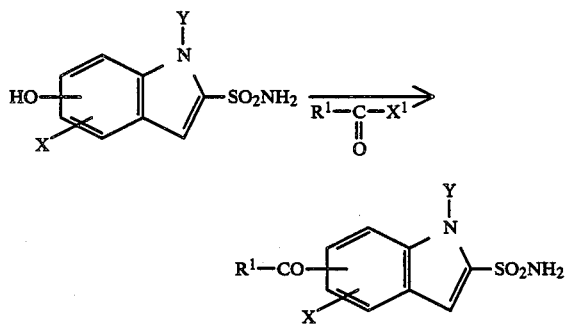

where $R^1$ has the meanings hereinbefore designated, and $X^1$ is chloro, bromo, iodo,

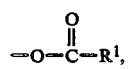

-continued

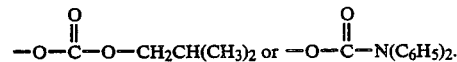

Generally equimolar amounts of the hydroxy-2-sulfamoyl-1H-indole and

are employed, although use of an excess of the more readily available reactant is satisfactory.

The reaction is conducted in a suitable, inert solvent such as acetone, dimethylformamide, pyridine, ethyl acetate, tetrahydrofuran or benzene and the like with at least an equimolar amount of a hydrohalide acceptor when the acylating agent is an acyl halide or with a carboxylic acid acceptor when the acylating agent is an acid anhydride. Bases such as triethylamine, pyridine and the like may be employed for this purpose.

The reaction may be conducted with or without a catalyst at temperatures of from 0° C. to the boiling point of the solvent used but preferably from about 15° C. to 50° C.

When a catalyst is employed, a 4,4-dialkylaminopyridine such as 4-dimethylaminopyridine or 4-pyrrolidinopyridine is preferred.

The compounds wherein R is

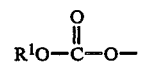

of this invention are most suitably prepared by reacting the compound

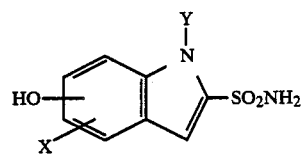

with an appropriate haloformate, particularly a chloroformate of the formula:

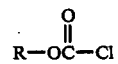

or a bis carbonate of the formula:

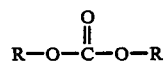

The reaction is conducted in a suitable solvent such as dimethylformamide, pyridine, acetone, ethyl acetate, tetrahydrofuran or benzene and the like with at least an equimolar amount of a hydrohalide acceptor. Bases such as triethylamine, pyridine and the like may be employed for this purpose.

The reaction may be conducted with or without a catalyst at temperatures of from 0° C. to the boiling point of the solvent used but preferably from 15° C. to 50° C.

When a catalyst is employed, triethylamine or a 4,4-dialkylaminopyridine such as 4-dimethylaminopyridine or 4-pyrrolidinopyridine is preferred.

In the novel process of this invention for preparing the ethers of hydroxy-2-sulfamoyl-1H-indole, the hydroxy compound is treated with an "alkylating" agent of formula $R^1$—$X^2$ wherein $X^2$ is a halide such as chloride, bromide or iodide, or other good leaving group such as mesylate, tosylate or benzenesulfonate in a suitable solvent such as dimethyl formamide, hexamethyl phosphoramide, or the like in the presence of a base such as an alkali metal alkoxide, preferably sodium methoxide, at about 0° C. to 35° C., usually about room temperature for about 10 to 30 hours.

An alternate synthesis of ethers comprises protecting the sulfonamide group as an N,N-disubstituted formamidine which is removed after formation of the desired ether. The formamidine derivative is prepared by adding, for example, N,N-dimethylformamide dimethylacetal to a suspension of the hydroxy-2-sulfamoyl-1H-indole in an inert organic solvent such as acetonitrile at about −10° to +35° C., preferably room temperature for about 0.5 to about 3 hours.

The ethers are then readily prepared by treating the hydroxy compound with the "alkylating" agent, $R^1$—$X^2$, in a solvent such as dimethyl sulfoxide, preferably in the presence of an acid acceptor such as potassium carbonate or the like, pyridine or the like or basic ion exchange resin. The reaction is conducted at about 25° to 100° C., preferably about 60° C., for about 10 to 36 hours, preferably about 18 hours.

The protecting group is then removed from the sulfonamide by treating the compound with dilute alkali such as 2N sodium hydroxide at about 20° to 60° C., preferably about 40° C. for about 0.5 to 3 hours, preferably about 1 hour. Also, 6N HCl at about 100° C. for 2–5 hours can be used to effect the desired deprotection.

The novel compounds of this invention with no substituent, i.e. R=H and those carrying fairly stable substituents such as wherein R is $R^1$ and $R^1$ is alkyl, cycloalkyl, cycloalkyl-alkyl, alkylcycloalkyl, alkoxyalkyl, alkenyl; R is $R^1$—O— wherein $R^1$ is as defined above; R is $R^5R^6$—N— wherein $R^5$ and $R^6$ are not hydrogen are conveniently prepared by formation of the sulfonamide group on the intact indole moiety in which the indole N is protected. This is accomplished by the procedure described earlier for preparation of methoxy-2-sulfamoylindoles.

The O-sulfates of this invention are prepared by reacting an hydroxy-2-sulfamoyl-1H-indole with sulfamic acid in pyridine at elevated temperatures (about 50° to the boiling point) for about 18 to 48 hours to provide the ammonium salt followed, if desired, by titration with hydroxides of the formula MOH to provide the other salts.

Similarly the O-phosphates of this invention are prepared by treatment of a hydroxy-2-sulfamoyl-1H-indole with phosphorus oxychloride, an alkyl dichlorophosphate or a dialkyl chlorophosphate in pyridine or similar basic solvent at about −5° to +5° C. for about 0.25 to 1.0 hour.

EXAMPLE 1

5-Hydroxy-1H-indole-2-sulfonamide

Step A: Preparation of 5-Methoxy-1-benzenesulfonylindole

To a solution of 5-methoxyindole (20.0 gm, 0.1368 mol) in dry THF (300 ml) containing 2,2'-dipyridyl (5.0 mg) under nitrogen at −78° C. was added via dropping funnel over 15 minutes n-butyllithium (1.6M in hexane, 95.0 ml, 0.15 mol). The cooling bath was removed and the solution stirred and allowed to warm to 0° C. over 1.0 hour. The mixture was recooled to −78° C., benzenesulfonyl chloride (25.36 gm, 0.1436 mol) was added via syringe over 15 minutes. During the addition the temperature did not rise above −60° C. The colorless mixture was allowed to warm slowly to room temperature overnight.

The reaction mixture was poured into 2% aqueous sodium bicarbonate (500 ml), and extracted with diethylether (4×200 ml). The combined extracts were washed with 2% aqueous sodium bicarbonate (2×150 ml), water (2×150 ml), brine 2×150 ml), and dried (MgSO₄). The diethylether was removed via vacuum and the light amber oil was triturated with 2:1 (V:V) hexane-ether to yield 33.85 gm of a tan solid, (86.11% yield), m.p. 95°–98° C.

Step B: Preparation of Lithium 5-methoxy-1-benzenesulfonylindole-2-sulfinate 5-Methoxy-1-benzenesulfonylindole (85.0 gm, 0.3 mole) was added to dry THF (300 ml) under nitrogen. The reaction was cooled to −78° C. and n-butyllithium (1.6M in hexane, 194.0 ml, 0.31 mole) was added dropwise over 1 hour. The reaction was stirred for 330 minutes.

Dry SO₂ gas was introduced onto the surface of the suspension. After the addition of the SO₂ gas (30 minutes), the reaction mixture was allowed to warm to room temperature. The reaction was diluted with hexane (500 mls) and the precipitate collected via vacuum filtration. The solid, after drying, yielded 100 gms (95% yield) of the lithium sulfinate salt which was used in the next step without further purification.

Step C: Preparation of 5-Methoxy-1-benzenesulfonyl-2-sulfamoylindole

Lithium 5-methoxy-1-benzene sulfonylindole-2-sulfinate (100 gm, 0.28 mole) was added to methylene chloride (350 ml) with cooling (5° C.). N-chlorosuccinimide (39.2 gm, 0.29 mole) was added portionwise to the reaction solution. The reaction was stirred for 2.0 hours.

The reaction mixture was filtered and the filtrate washed with methylene chloride (400 ml). The solvent was removed under vacuum to yield a brown oil.

The oil was dissolved in THF (200 ml), cooled (5° C.), and dry NH₃ gas bubbled through the reaction solution. The excess ammonia and THF were removed under vacuum to yield a brown solid. The solid was triturated with water to yield 85.6 gm (90.0%) of 5-methoxy-1-benzenesulfonyl-2-sulfamoylindole. A portion was recrystallized from absolute ethanol mp 188°–189° C.

Step D: Preparation of 5-Methoxy-2-sulfamoyl-1H-indole 5-methoxy-1-benzenesulfonyl-2-sulfamoylindole (22.0 gm, 0.97 mmol) was dissolved in 10% sodium hydroxide (250 ml) and warmed to 90° C. for 1 hour. The cooled reaction mixture was extracted with ethyl acetate (2×150 ml) and neutralized with concentrated hydrochloric acid. The precipitate was collected via filtration and the filtrate was extracted with ethyl acetate (4×200 ml). The precipitate collected earlier was combined with the extracts and the extracts were washed with water (2×100 ml), brine (2×100 ml) and dried (MgSO4). The organic solvent was removed under vacuum to yield a brown solid 10.2 gm. The solid was recrystallized from water using decolorizing carbon to yield white crystals; 4.5 gm., m.p. 208°–209° C.
Anal, calculated for $C_9H_{10}N_2O_3S$: C, 47.77; H, 4.46; N, 12.38
Found: C, 47.75; H, 4.49; N, 12.29

Step E: Preparation of 5-hydroxy-2-sulfamoyl-1H-indole

5-Methoxy-2-sulfamoyl-1H-indole (2.5 gm, 11 mmol) was mixed with pyridine hydrochloride (7.5 gm) and heated neat at 190° C. for 30 minutes. The reaction was cooled to 140° C. and poured onto ice water (25 gm). The mixture was extracted with ethyl acetate (3×100 ml), washed with water (2×50 ml), brine (2×25 ml) and dried (MgSO4). The ethyl acetate was removed under vacuum to yield a brown solid 2.4 gm. The solid was flash chromatographed using silica gel with 95/5 (V/V) chloroform-methanol. The isolated compound was crystallized using chloroform-methanol 95/5 (V/V) to yield a white solid; 628 mg., m.p. 220°–221° C. (dec).
Anal: Calculated for $C_8H_8N_2O_3S$: C, 45.27; H, 3.80; N, 13.26
Found: C, 45.20; H, 3.88; N, 13.26.

EXAMPLE 2

6-Hydroxy-1H-indole-2-Sulfonamide

Step A: Preparation of 6-Methoxy-1-benzenesulfonylindole

6-Methoxyindole (16.0 gm, 0.1095 m) was added to a round bottomed flask along with 150 ml of dry tetrahydrofuran and 2,2'-dipyridyl (5.0 mg) as a color indicator. The reaction flask was cooled to −78° C. using a dry ice/acetone bath. A solution of 1.6M N-butyllithium in hexane (71.9 ml, 0.1150 m) was added dropwise over about 30 minutes. A red color persisted. The dry ice/acetone bath was removed and the reaction allowed to warm to 0° C. over about 45 minutes. The reaction flask was then cooled to −78° C. and benzenesulfonyl chloride (21.3 gm, 0.1205 m) was added dropwise over 15 minutes with stirring. The reaction was allowed to warm to room temperature over 2 hours.

The reaction was poured onto 500 ml of 2% (W/V) sodium carbonate solution and extracted with diethylether (4×200 ml). The combined extracts were washed with saturated sodium carbonate solution (2×100 ml), water (2×100 ml), brine (2×100 ml) and dried (K2CO3). The mixture was filtered and the diethylether removed via vacuum to yield a white solid 25.0 gm.

Step B: Preparation of Lithium 6-methoxy-1-benzenesulfonylindole-2-sulfinate 6-methoxy-1-benzenesulfonylindole (500 gm, 0.17 mole) was added to dry THF, under a nitrogen atmosphere. The reaction was cooled to −78° C. and n-butyllithium (1.6N in hexane, 115.0 ml, 18 mole) was added dropwise over 1.0 hour. The reaction was stirred for 30 minutes after the addition.

Dry SO2 gas was applied to the surface of the suspension. After 15 minutes the SO2 was discontinued. The reaction was allowed to warm to room temperature over 2 hours. The raction was diluted with hexane (500 mls) and the white precipitate removed via filtration to give 60.0 gm (96.5% yield) of the lithium sulfinate salt which was used without further purification.

Step C: Preparation of 6-Methoxy-2-sulfamoyl-1H-indole

Lithium-6-methoxy-1-benzenesulfonylindole-2-sulfinate (60.0 gm, 0.17 mole) was added to methylene chloride (200 ml) with cooling (5° C.). N-chlorosuccinimide (24.0 gm, 0.18 mole) was added portionwise to the reaction solution. The reaction was stirred for 2 hours.

The reaction mixture was filtered and the filtrate washed with methylene chloride (300 ml). The solvent was removed under vacuum to yield a brown oil.

The oil was dissolved in THF (500 ml), cooled (5° C.), and dry NH3 gas bubbled through the reaction solution. The excess ammonia and THF were removed under vacuum to yield a brown solid. The solid was triturated with water to yield 51.5 gm (89.2%) of a brown solid. A sample was recrystallized from abs. ethanol; mp 171°–172° C.

Step D: Preparation of 6-Hydroxy-2-sulfamoyl-1H-indole

6-Methoxy-2-sulfamoyl-1H-indole (3.0 gm, 13.0 mmol) was added to pyridine hydrochloride (15.0 gm) and the mixture heated to 190° C. for 1.0 hour. The hot reaction mixture was poured onto ice/brine (50 gm/50 ml) and extracted with ethyl acetate (3×150 ml). The combined extracts were washed with water (2×25 ml), brine (2×25 ml) and dried (MgSO4). The solvent was removed under vacuum to yield a tan solid (1.9 gm, 69% yield). Column chromatography over silica gel with 95:5 (V/V) chloroform:methanol afforded 1.41 gm of a tan solid. Crystallization from chloroform-methanol (95:5 (V/V) gave an analytical sample, m.p. 194°–195° C.
Anal: Calc'd for $C_8H_8N_2O_3S$: C, 45.27; H, 3.80; N, 13.20
Found: C, 45.25; H, 3.89; N, 13.18

EXAMPLE 3

5,6-Methylenedioxy-2-sulfamoylindole

Step A: Preparation of 5,6-Methylenedioxy-1-benzenesulfonylindole

To a solution of 5,6-methylenedioxyindole (11.5 gm, 71 mmol) in freshly distilled tetrahydrofuran (60 ml) under a nitrogen atomosphere at −70° C. was added dropwise 1.6M n-butyllithium (50 ml, 80 mmol) over a one-half hour period. Then benzenesulfonyl chloride (10.5 ml, 82 mmol) was added dropwise. The reaction mixture was gradually warmed to room temperature and poured into water/methylene chloride The methylene chloride layer was separated, dried (anhydrous Na2So4), filtered and evaporated to give 23.4 gm of crude product. This solid was triturated with diethyl ether and the purified product collected by filtration (18.0 gm), mp 142°–145° C.

Step B: Preparation of lithium 5,6-methylenedioxy-1-benzenesulfonylindole-2-sulfinate 5,6-Methylenedioxy-1-benzenesulfonylindole (4.05 gm, 13.5 mmol) was dissolved in freshly distilled tetrahydrofuran (30 ml) under nitrogen cooled to −70° C., and to it was added dropwise 1.6M butyllithium in hexane (9.0 ml, 14.4 mmol). After one-half hour sulfur dioxide gas was bubbled over the surface of the reaction as the reaction slowly warmed to room temperature.

Addition of hexane (60 ml) to the reaction caused the sulfinate salt to precipitate. This salt was collected by filtration, washed with hexane and air-dried to give 5.6 gm of solid which was used as is.

Step C: Preparation of 5,6-Methylenedioxy-1-benzenesulfonylindole-2-sulfonyl chloride Lithium 5,6-methylenedioxy-1-benzene sulfonylindole-2-sulfinate (5.3 gm) was dissolved in methylene chloride (50 ml), cooled in an ice bath to 5° C. and N-chlorosuccimide (1.85 gm, 13.5 mmol) solid was added. After stirring for 1 hour the reaction mixture was warmed to room temperature and the precipitated lithium succinimide removed by filtration. The methylene chloride solution was evaporated and the residue triturated with diethyl ether to give 3.66 gm of product, mp 148°–150° C.

Step D: Preparation of 5,6-Methylenedioxy-1-benzenesulfonyl-2-sulfamoylindole A solution of 5,6-methylenedioxy-1-benzenesulfonylindole-2-sulfonyl chloride (3.66 gm, 9.15 mmol) in acetone (35 ml) was added dropwise to a solution of concentrated ammonium hydorxide (5 ml) in acetone (20 ml) which was cooled in an ice bath. After 1 hour the reaction was warmed to room temperature and the solvent was evaporated. The residue was suspended in cold water and crystalline solid was collected by filtration. This solid was dissolved in ethyl acetate, dried (anhydrous Na$_2$SO$_4$), evaporated, and the residue was triturated with diethyl ether to give crystalline product (1.75 gm), mp 229°–232° C.

Step E: Preparation of 5,6 Methylenedioxy-2-sulfamoylindole

An initial suspension of 5,6-methylenedioxy-1-benzenesulfonyl-2-sulfamoylindole (2.21 gm, 5.8 mmol) in 40% sodium hydroxide (4 ml, 40 mmol) and water (11 ml) was warmed at 90° C. for 1 hour to give a homogeneous solution. The reaction was cooled to room temperature and the product salt precipitated. This mixture was acidified with conc. HCl and the precipitated producted collected by filtration. This solid was dissolved in ethyl acetate/acetonitrile, and dried (anhydrous Na$_2$SO$_4$). This solution was filtered through a charcoal pad and the solvents evaporated. The residue was triturated with diethyl ether to give the crystalline product (1.1 gm), mp 234°–237° C.

For use in treatment of conditions relieved by the inhibition of carbonic anhydrase, the active compound can be administered either systemically, or, in the treatment of the eye, topically. The dose administered can be from as little as 0.1 to 25 mg or more per day, singly, or preferably on a 2 to 4 dose per day regimen although a single dose per day is satisfactory.

When administered for the treatment of elevated intraocular pressure or glaucoma, the active compound is most desirably administered topically to the eye, although systemic treatment is, as indicated, also possible.

When given systemically, the drug can be given by any route, although the oral route is preferred. In oral administration the drug can be employed in any of the usual dosage forms such as tablets or capsules, either in a contemporaneous delivery or sustained release form. Any number of the usual excipients or tableting aids can likewise be included.

When given by the topical route, the active drug or an ophthalmologically acceptable salt thereof such as the sodium or potassium salt is formulated into an ophthalmic preparation. In such formulations, from 0.1% to 15% by weight can be employed. The objective is to administer a dose of from 0.1 to 10 mg per eye per day to the patient, with treatment continuing so long as the condition persists.

Thus, in an ophthalmic solution, insert, ointment or suspension for topical delivery, or a tablet, intramuscular, or intravenous composition for systemic delivery, the active medicament or an equivalent amount of a salt thereof is employed, the remainder being carrier, excipients, preservatives and the like as are customarily used in such compositions.

The active drugs of this invention are most suitably administered in the form of ophthalmic pharmaceutical compositions adapted for topical administration to the eye such as a suspension, ointment, or as a solid insert. Formulations of these compounds may contain from 0.01 to 15% and especially 0.5% to 2% of medicament. Higher dosages as, for example, about 10%, or lower dosages can be employed provided the dose is effective in reducing or controlling elevated intraocular pressure. As a unit dosage from between 0.001 to 10.0 mg, preferably 0.005 to 2.0 mg, and especially 0.1 to 1.0 mg of the compound is generally applied to the human eye, generally on a daily basis in single or divided doses so long as the condition being treated exists.

These hereinbefore described dosage values are believed accurate for human patients and are based on the known and presently understood pharmacology of the compounds, and the action of other similar entities in the human eye. They reflect the best mode known. As with all medications, dosage requirements are variable and must be individualized on the basis of the disease and the response of the patient.

The pharmaceutical preparation which contains the active compound may be conveniently admixed with a non-toxic pharmaceutical organic carrier, or with a non-toxic pharmaceutical inorganic carrier. Typical of pharmaceutically acceptable carriers are, for example, water, mixtures of water and water-miscible solvents such as lower alkanols or aralkanols, vegetable oils, polyalkylene glycols, petroleum based jelly, ethyl cellulose, ethyl oleate, carboxymethylcellulose, polyvinylpyrrolidone, isopropyl myristate and other conventionally employed acceptable carriers. The pharmaceutical preparation may also contain non-toxic auxiliary substances such as emulsifying, preserving, wetting agents, bodying agents and the like, as for example, polyethylene glycols 200, 300, 400 and 600, carbowaxes 1,000, 1,500, 4,000, 6,000 and 10,000, antibacterial components such as quaternary ammonium compounds, phenylmercuric salts known to have cold sterilizing properties and which are non-injurious in use, thimerosal, methyl and propyl paraben, benzyl alcohol, phenyl ethanol, buffering ingredients such as sodium chloride, sodium borate, sodium acetates, gluconate buffers, and other conventional ingredients such as sorbitan monolaurate, triethanolamine, oleate, polyoxyethylene sorbitan monopalmitylate, dioctyl sodium sulfosuccinate, monothioglycerol, thiosorbitol,ethylenediamine tetraacetic acid, and the like. Additionally, suitable ophthalmic vehicles can be used as carrier media for the present purpose including conventional phosphate buffer vehicle systems, isotonic boric acid vehicles, isotonic sodium chloride vehicles, isotonic sodium borate vehicles and the like.

The pharmaceutical preparation may also be in the form of a solid insert such as one which after dispensing the drug remains essentially intact, or a bio-erodible insert that either is soluble in lacrimal fluids, or otherwise disintegrates.

The following examples of ophthalmic formulations are given by way of illustration.

EXAMPLE 35

| 5-Hydroxy-2-sulfamoyl-1H—indole | 1 mg. | 15 mg. |
| --- | --- | --- |
| Monobasic sodium phosphate.2H2O | 9.38 mg. | 6.10 mg. |
| Dibasic sodium phosphate.12H2O | 28.48 mg. | 16.80 mg. |
| Benzalkonium chloride | 0.10 mg. | 0.10 mg. |
| Water for injection q.s. ad. | 1.0 ml. | 1.0 ml. |

Compound I, phosphate buffer salts, and benzalkonium chloride are added to and dissolved in water. The pH of the composition is adjusted to 6.8 and diluted to volume. The composition is rendered sterile by ionizing radiation.

EXAMPLE 36

| 6-(2-Sulfamoyl-1H—indolyl) 2-methylpropionate (II) | 5 mg. |
| --- | --- |
| petrolatum q.s. ad. | 1 gram |

Compound II and the petrolatum are aseptically combined.

EXAMPLE 37

| 5-(2-Sulfamoyll-H—indolyl) acetate | 1 mg. |
| --- | --- |
| Hydroxypropylcellulose q.s. | 12 mg. |

Ophthalmic inserts are manufactured from compression molded films which are prepared on a Carver Press by subjecting the powdered mixture of the above ingredients to a compressional force of 12,000 lbs. (gauge) at 300° F. for one to four minutes. The film is cooled under pressure by having cold water circulate in the platen. Ophthalmic inserts are then individually cut from the film with a rod-shaped punch. Each insert is placed into a vial, which is then placed in a humidity cabinet (88% R.H. at 30° C.) for two or four days. After removal from the humidity cabinet, the vials are stoppered and then capped. The vials containing the hydrate insert are then autoclaved at 250° F. for ½ hour.

EXAMPLE 38

| 6-(2-Sulfamoyl-1H—indolyl) acetate | 1 mg. |
| --- | --- |
| Hydroxypropyl cellulose q.s. ad. | 12 mg. |

Ophthalmic inserts are manufactured from a solvent cast film prepared by making a viscous solution of the powdered ingredients listed above using methanol as the solvent. The solution is placed on a Teflon plate and allowed to dry at ambient conditions. After drying, the film is placed in an 88% R.H. cabinet until it is pliable. Appropriately sized inserts are cut from the film.

EXAMPLE 39

| 5-Hydroxy-2-sulfamoyl-1H—indole | 1 mg. |
| --- | --- |
| Hydroxypropylmethyl cellulose q.s. ad. | 12 mg. |

Ophthalmic inserts are manufactured from a solvent cast film which is prepared by making a viscous solution of the powdered blend of the above ingredients using a methanol/water solvent system (10 ml. methanol is added to 2.5 g. of the powdered blend, to which 11 ml. of water (in three divided portions) is added. The solution is placed on a Teflon plate and allowed to dry at ambient conditions. After drying, the film is placed in an 88% R.H. cabinet until it is pliable. Appropriately sized inserts are then cut from the film.

EXAMPLE 40

| 6-(2-Sulfamoyl-1H—indolyl) acetate | 1 mg. |
| --- | --- |
| Hydroxypropylmethyl cellulose q.s. ad. | 12 mg. |

Ophthalmic inserts are manufactured from compression molded films which are prepared on a Carver Press by subjecting the powdered mixture of the above ingredients to a compressional force of 12,000 lbs. (gauge) at 350° F. for one minute. The film is cooled under pressure by having cold water circulate in the platen. Ophthalmic inserts are then individually cut from the film with a punch. Each insert is placed into a vial, which is then placed in a humidity cabinet (88% R.H. at 30° C.) for two to four days. After removal from the humidity cabinet, the vials are stoppered and then capped. The vials containing the hydrated insert are then autoclaved at 250° F. for one-half hour.

It is highly preferred that the solid inserts of this invention are available for use by the patient in a pathogen free condition. Thus, it is preferred to sterilize the inserts and to insure against recontamination, the sterilization is preferably conducted after packaging. The best mode of sterilizing is to employ ionizing radiation including radiation emanating from Cobalt 60 or high energy electron beams.

What is claimed is:

1. A method of treating glaucoma and elevated intraocular pressure which comprises topical ocular application to a patient in need of such treatment of an effective intraocular pressure lowering amount of a compound with structural formula:

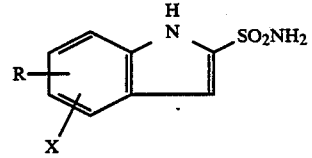

or an ophthalmologically acceptable salt thereof, wherein X is hydrogen, R is HO—,

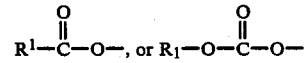

wherein $R^1$ is $C_{1-5}$alkyl.

2. The method of claim 1, wherein the compound is:
5 (or 6)-hydroxy-2-sulfamoyl-1H-indole;
5 (or 6)-(2-sulfamoyl-1H-indolyl) acetate;
5 (or 6)-(2-sulfamoyl-1H-indolyl) 2,2-dimethylpropionate; or
5 (or 6)-(2-sulfamoyl-1H-indolyl) 2-methylpropionate.

* * * * *